United States Patent
Bauer

[19]

[11] Patent Number: 5,915,615
[45] Date of Patent: *Jun. 29, 1999

[54] TISSUE FASTENING DEVICE

[76] Inventor: William Bauer, Newnan Medical Plaza, Suite 204, 58 Hospital Rd., Newnan, Ga. 30263

[ * ] Notice: This patent issued on a continued prosecution application filed under 37 CFR 1.53(d), and is subject to the twenty year patent term provisions of 35 U.S.C. 154(a)(2).

[21] Appl. No.: 08/728,430

[22] Filed: Oct. 9, 1996

Related U.S. Application Data

[63] Continuation of application No. 08/294,928, Aug. 24, 1994, abandoned, which is a continuation-in-part of application No. 08/035,809, Mar. 23, 1993, Pat. No. 5,351,871, which is a continuation-in-part of application No. 07/858,028, Mar. 26, 1992, Pat. No. 5,370,294.

[51] Int. Cl.$^6$ ..................................................... A61B 17/04
[52] U.S. Cl. ................................... 227/177.1; 227/175.1; 227/181.1; 227/15; 227/19
[58] Field of Search ................................ 227/19, 18, 15, 227/175.1, 176.1, 177.1, 181.1, 901

[56] References Cited

U.S. PATENT DOCUMENTS

| | | | |
|---|---|---|---|
| D. 279,501 | 7/1985 | Spreckelmeier et al. | D24/26 |
| D. 301,740 | 6/1989 | Green | D24/27 |
| 661,598 | 11/1900 | Callison et al. | 72/410 |
| 2,853,074 | 9/1958 | Olson | 227/177 |
| 3,082,426 | 3/1963 | Miles | 606/143 |
| 3,278,107 | 10/1966 | Rygg | 227/143 |
| 3,470,875 | 10/1969 | Johnson | 606/145 |
| 3,575,038 | 4/1971 | Mallett | 72/410 |
| 4,402,445 | 9/1983 | Green | 227/15 X |
| 4,506,670 | 3/1985 | Crossley | 227/15 X |
| 4,615,474 | 10/1986 | Strekopytov et al. | 227/19 |
| 4,633,861 | 1/1987 | Chow et al. | 128/305 |
| 4,784,137 | 11/1988 | Kulik et al. | 128/334 R |
| 4,991,764 | 2/1991 | Mericle | 227/178 |
| 5,040,715 | 8/1991 | Green et al. | 227/176 |
| 5,125,553 | 6/1992 | Oddsen et al. | 227/175 |
| 5,156,614 | 10/1992 | Green et al. | 227/176.1 X |
| 5,351,871 | 10/1994 | Bauer | 227/177.1 |
| 5,352,238 | 10/1994 | Green et al. | 227/176.1 X |
| 5,366,134 | 11/1994 | Green et al. | 227/176.1 |
| 5,370,294 | 12/1994 | Bauer | 227/177.1 |
| 5,423,858 | 6/1995 | Bolanos et al. | 606/220 |

*Primary Examiner*—Rinaldi I. Rada
*Assistant Examiner*—Boyer Ashley
*Attorney, Agent, or Firm*—Pillsbury Madison & Sutro LLP

[57] ABSTRACT

A manually operated fastener driving device including first and second arm assemblies, each of the arm assemblies having a distal portion and a proximal portion, the proximal portion of the first arm assembly being pivotally coupled to the proximal portion of the second arm assembly; a fastener capsule associated with the first arm assembly and being constructed and arranged at the distal portion thereof so as to be movable between an inoperative position and an operative position; a plurality of fasteners carried by the first arm assembly, each fastener being constructed and arranged to be individually received within the fastener capsule, the first arm assembly including a first actuator constructed and arranged to move the fastener capsule from its inoperative position to its operative position; a plurality of fastener receptacles carried by the second arm assembly, a leading receptacle of the plurality of receptacles being selectively disposed to receive and engage a fastener; and a handle assembly coupled to the proximal portions of the first and second arm assemblies, the handle assembly being cooperable with the first actuator such that manual actuation of the handle assembly (1) moves the fastener capsule with a fastener therein from its inoperative position to its operative position and (2) moves the distal portions of the first and second arm assemblies towards each other so as to retain the fastener within the leading receptacle.

22 Claims, 9 Drawing Sheets

TISSUE FASTENING DEVICE

This is a continuation of application Ser, No. 08/294,928, filed on Aug. 24, 1994, now abandoned. This application is a continuation-in-part of application Ser. No. 08/035,809 filed Mar. 23, 1993 now U.S. Pat No. 5,351,871, which is a continuation-in-part of application Ser. No. 07/858,028 filed Mar. 26, 1992 now U.S. Pat. No. 5,370,294.

BACKGROUND OF THE INVENTION

1. Field of the Invention

This invention relates to a device for fastening human tissue, and, more particularly, to an intranasal fastener driving device for insertion into the narrow passages of the nose for dispensing fasteners into septal tissue.

2. Description of Related Art

Septal surgery is among the most common operations performed. It is estimated that 500,000 septal surgeries are performed each year in the United States by Otolaryngologists and Plastic Surgeons.

Septal surgery was first described in 1882, and the techniques have been modified up to the present day to correct the septum and preserve as much cartilage as possible to prevent loss of support and saddling of the external nose. Submucous resection and septoplasty are performed for nasal obstruction, sinusitis, and headache. It is often performed in conjunction with rhinoplasty for cosmetic results.

Traditional septal surgery begins with an intranasal incision through the lining of the septum. The lining is then elevated away from the supporting skeleton by creating a tunnel on one or both sides of the septum. This allows direct visualization of the distorted bone or cartilage. Repair consists of removing or contouring the bone and cartilage. Support is assured by preserving as much cartilage as possible or by replacing crooked pieces of cartilage with straight pieces. Upon completion, the septum is conventionally held together with packing or suturing to prevent hematoma formation. However, intranasal packing is generally left in place 24–72 hours and causes a great deal of discomfort to the patient. Further, studies have shown that intranasal packing reduces oxygen saturation and can cause toxic shock syndrome. Therefore, intranasal packing is not a benign procedure. Unfortunately, its alternative, intranasal suturing, is technically difficult and sometimes impossible to perform

SUMMARY OF THE INVENTION

In accordance with the principles of the present invention, intranasal fastening is employed as an adjunct to, or replacement of, intranasal packing following submucous resection of the septum or its variation, septoplasty. Intranasal septal fastening is performed so as to support the septal tissue until healing commences. Thus, intranasal septal fastening in accordance with the invention is accomplished by providing a fastener driving device capable of passing a fastener, such as a staple or other mechanical fasteners, through the loose mucosa of the septum and anchoring it to septal tissue. Other similar mechanical fasteners suitable for stapling, attaching, and mechanical suturing or for coaption of two surfaces by a third bonding material requiring a mechanical device for introduction into and delivery within small cavities, are within the contemplation of the invention. Such a procedure may mean simply joining two mucosal surfaces and allowing them to heal together as a single unit. Intranasal septal fastening may also be used in accordance with the invention to hold and secure cartilage or bone between the two mucosal membranes for added support. In the same manner, tissue grafts can be secured to the septum for repair of septal perforations.

Intranasal fastening in accordance with the invention offers two significant advantages. First, the procedure is comfortable for the patient; it can avoid complete nasal obstruction, thus reducing the likelihood of headaches and sinus pressure which may occur when intranasal packing is performed. Secondly, for the trained surgeon, intranasal fastening can be performed easily and can be an extremely quick procedure which saves operating time.

Devices have been developed to apply fasteners such as staple sutures. For example, U.S. Pat. Nos. 3,575,038 and 3,278,107 disclose devices for applying staple sutures to body tissue. These devices, however, are not suited for intranasal fastening since the fastener arms are too large to be inserted into and pass along the narrow, nasal cavity.

More particularly, the depth of a human nasal cavity from front to back is about 7 cm in adults. The greatest depth in the nose required for fastening is approximately 5 cm. The width of the septum varies approximately from 1 cm at the columellar entrance to 4 mm throughout the rest of the nose. The distance between the outer walls of the two nasal passages is about 2 cm at the outer nares entrance and 13 cm at the pyriform aperture or inner nares. The average width of each nasal passage is about 5 mm.

After septoplasty the length of a fastener should be in the range of approximately 3 mm to 5 mm. A 3 mm fastener will not generally penetrate the mucosal wall, but may still provide a fastening function. If the fastener has a length of 5 mm, 3 mm thereof may extend into the mucosal wall and the remaining 2 mm thereof, which extends beyond a surface of the wall, may be either crimped or otherwise retained.

Conventional stapling or fastener driving devices cannot be used for septal fastening since they are not constructed and arranged to be inserted into a nasal passage and thereafter deliver a fastener therein.

Thus, an object of the invention is to provide an intranasal fastener driving device which can be accommodated by the narrow nasal passages to perform a fastening process and then be removed easily from the passages. In accordance with the principles of the present invention, this and other objects are achieved by providing a preferably manually operated fastener driving device including first and second arm assemblies, each of the arm assemblies having a distal portion and a proximal portion, with the proximal portion of the first arm assembly being pivotally coupled to the proximal portion of the second arm assembly. A fastener capsule is associated with the first arm assembly and is constructed and arranged at the distal portion thereof so as to be movable between an inoperative position and an operative position. A plurality of fasteners are carried by the first arm assembly, each fastener being constructed and arranged to be individually received within the fastener capsule. The first arm assembly includes a first actuator constructed and arranged to move the fastener capsule from its inoperative position to its operative position. Moreover, a plurality of fastener receptacles are carried by the second arm assembly, a leading receptacle of the plurality of receptacles being selectively disposed to receive and engage a fastener. A handle assembly is coupled to the proximal portions of the first and second arm assemblies, the handle assembly being cooperable with the first actuator such that manual actuation of the handle assembly (1) moves the fastener capsule with a fastener therein from its inoperative position to its operative position and (2) moves the distal portions of the first and second arm assemblies towards each other so as to retain the fastener within the leading receptacle. The capsule functions as a trocar allowing a relatively soft, bioabsorbable fastener to be passed through resilient tissue in the body, such as cartilage.

DETAILED DESCRIPTION OF THE INVENTION

Referring to the drawings, an intranasal septal fastener driving device, generally indicated at 10, which embodies the principles of the present invention, is shown.

The fastener driving device 10 includes an upper arm assembly, generally indicated at 12, a receptacle arm assembly, generally indicated at 14 disposed below the upper arm 12, a handle assembly or actuating means, generally indicated at 16 coupled to the upper arm assembly 12 and the receptacle arm assembly 14, and a housing assembly 18. The housing assembly 18 includes two mating parts 17 and 19 which house the handle assembly 16, as will be appreciated below.

Figures 2, 3:
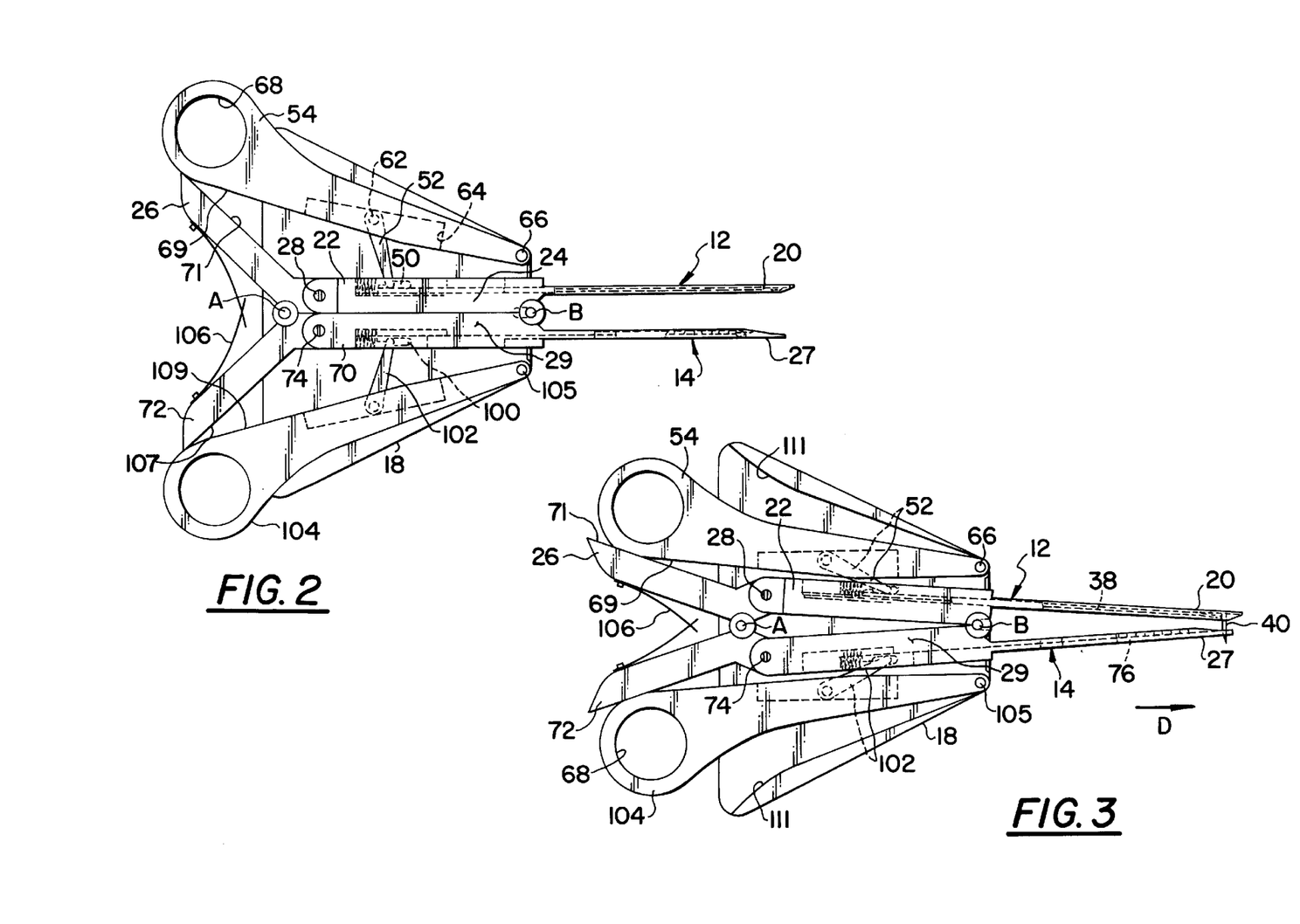
FIG. 2 is a front view of the device of FIG. 1, shown with portions of the device removed for clarity of illustration and shown with the handles and arm assemblies in an inoperative position.
FIG. 3 is a front view of the fastener driving device of FIG. 2, shown with the handles and arm assemblies in an operative position.
Figure 4:
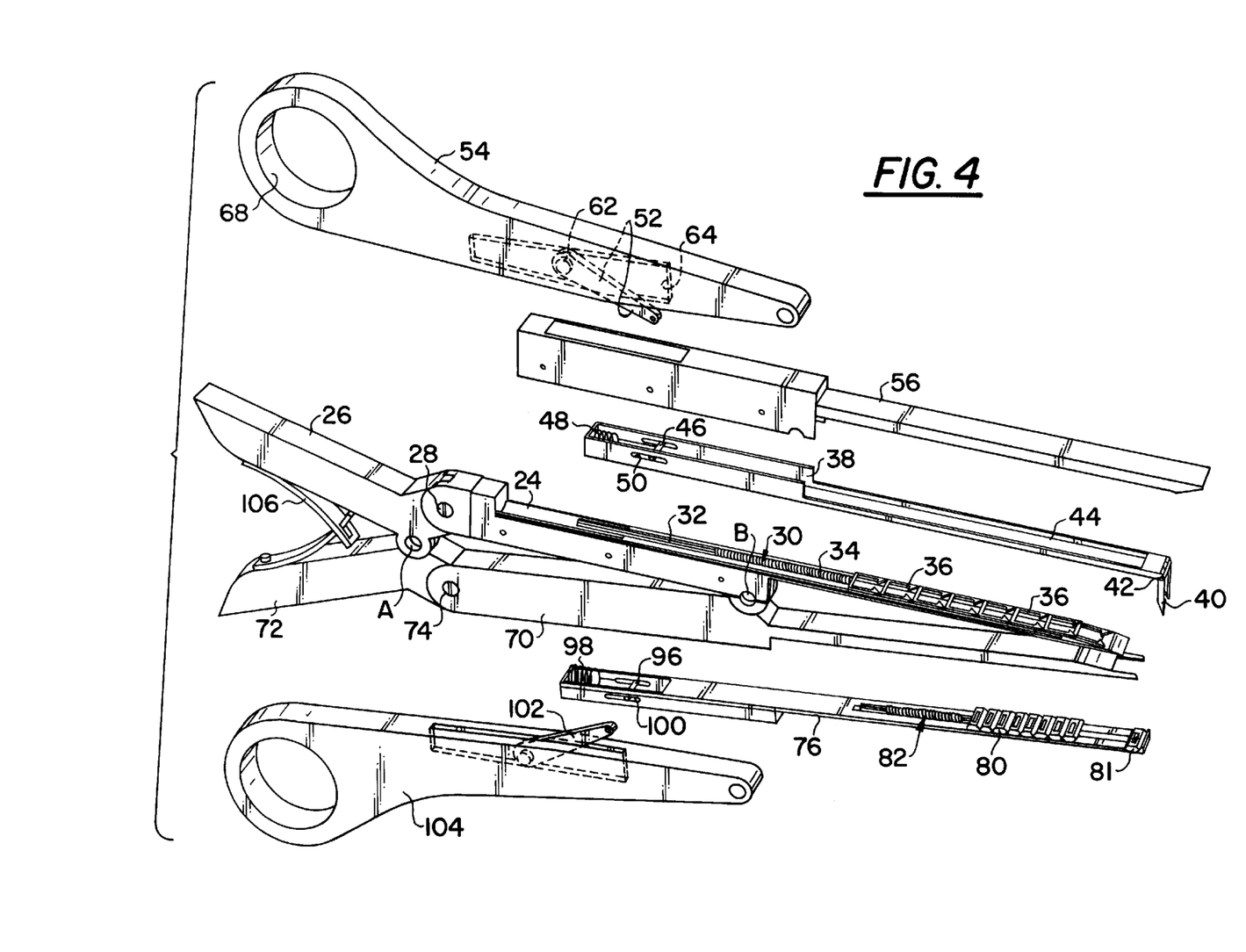
FIG. 4 is an exploded view of the intranasal fastener driving device of FIG. 1, shown without the housing for clarity of illustration.
Figure 5:
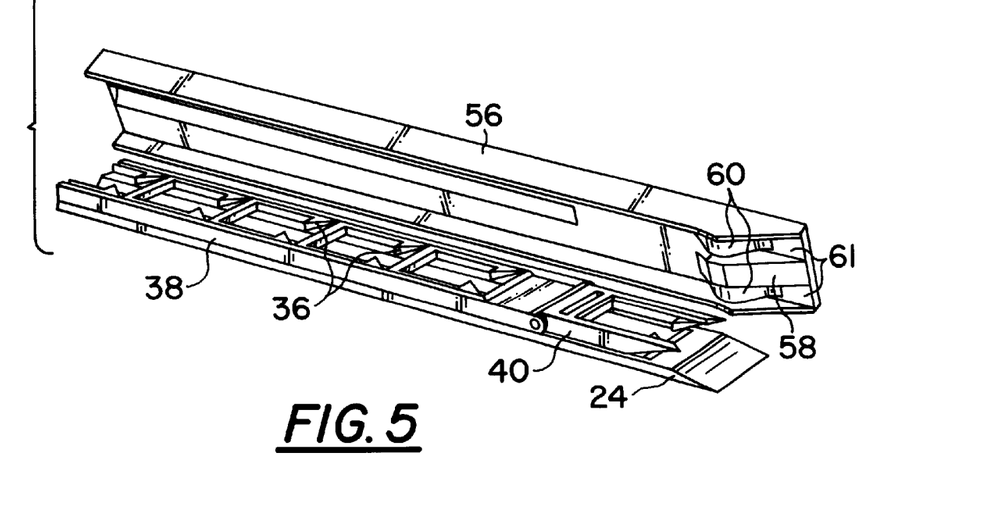
FIG. 5 is a partial exploded view of an upper arm assembly of the device, shown with a fastener capsule in an inoperative position.
Figure 6:
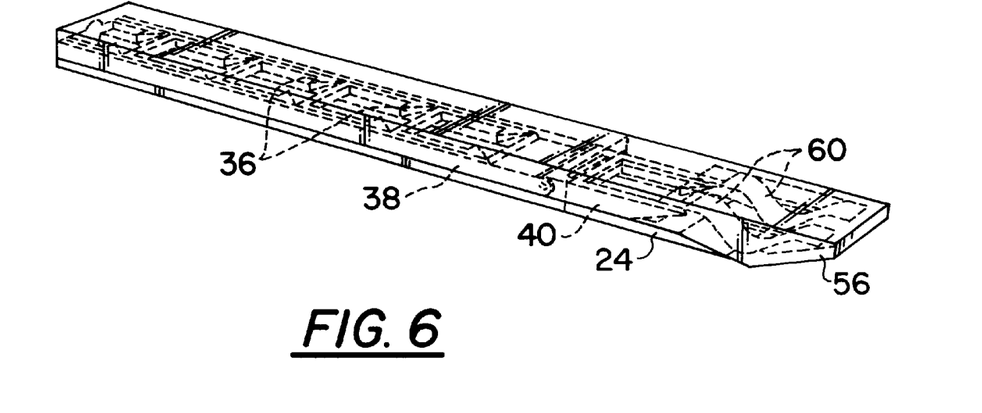
FIG. 6 is an partial exploded view of the upper arm assembly of FIG. 5, shown in an assembled condition.
Figure 7:
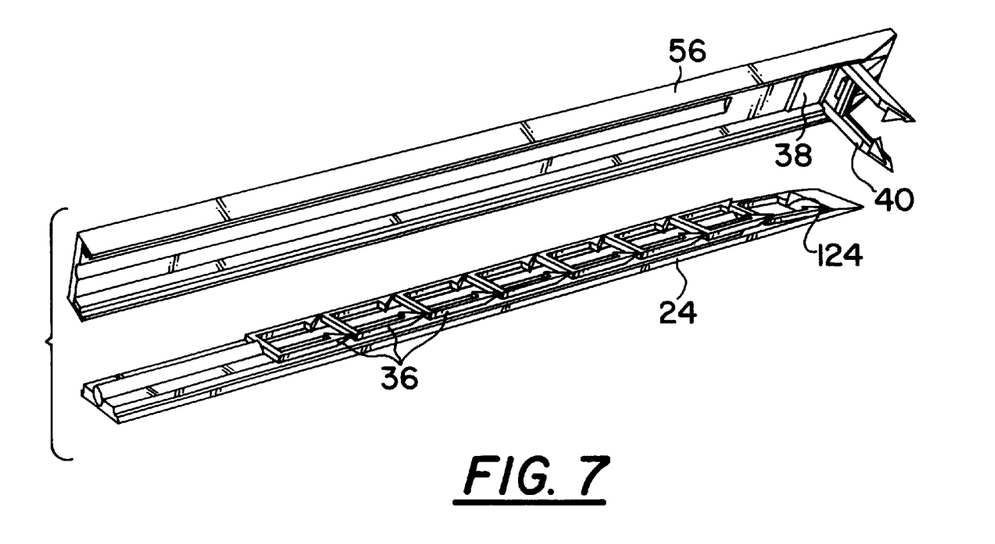
FIG. 7 is a partial exploded view of the upper arm assembly of FIG. 5, shown with the fastener capsule in an operative position.
Figure 8:
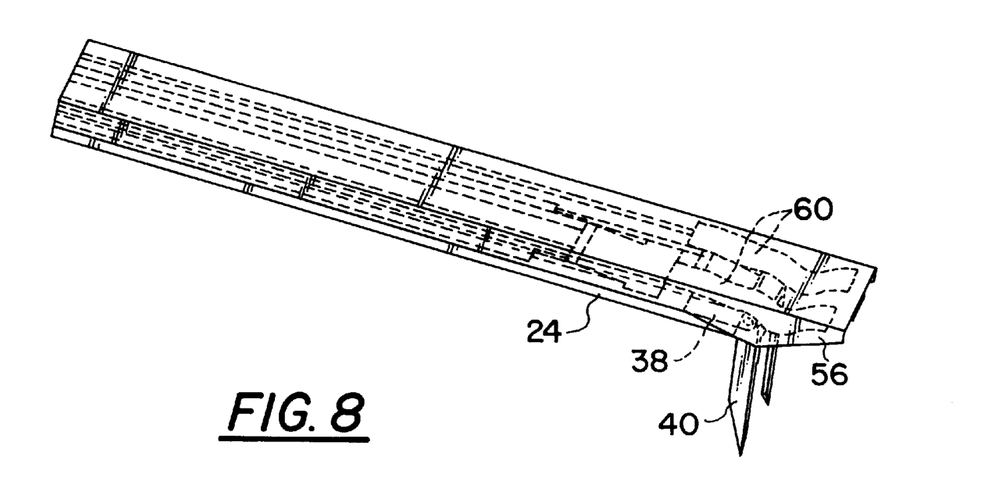
FIG. 8 is a partial perspective view of the upper arm assembly of FIG. 7, shown in an assembled position.
Figure 13:
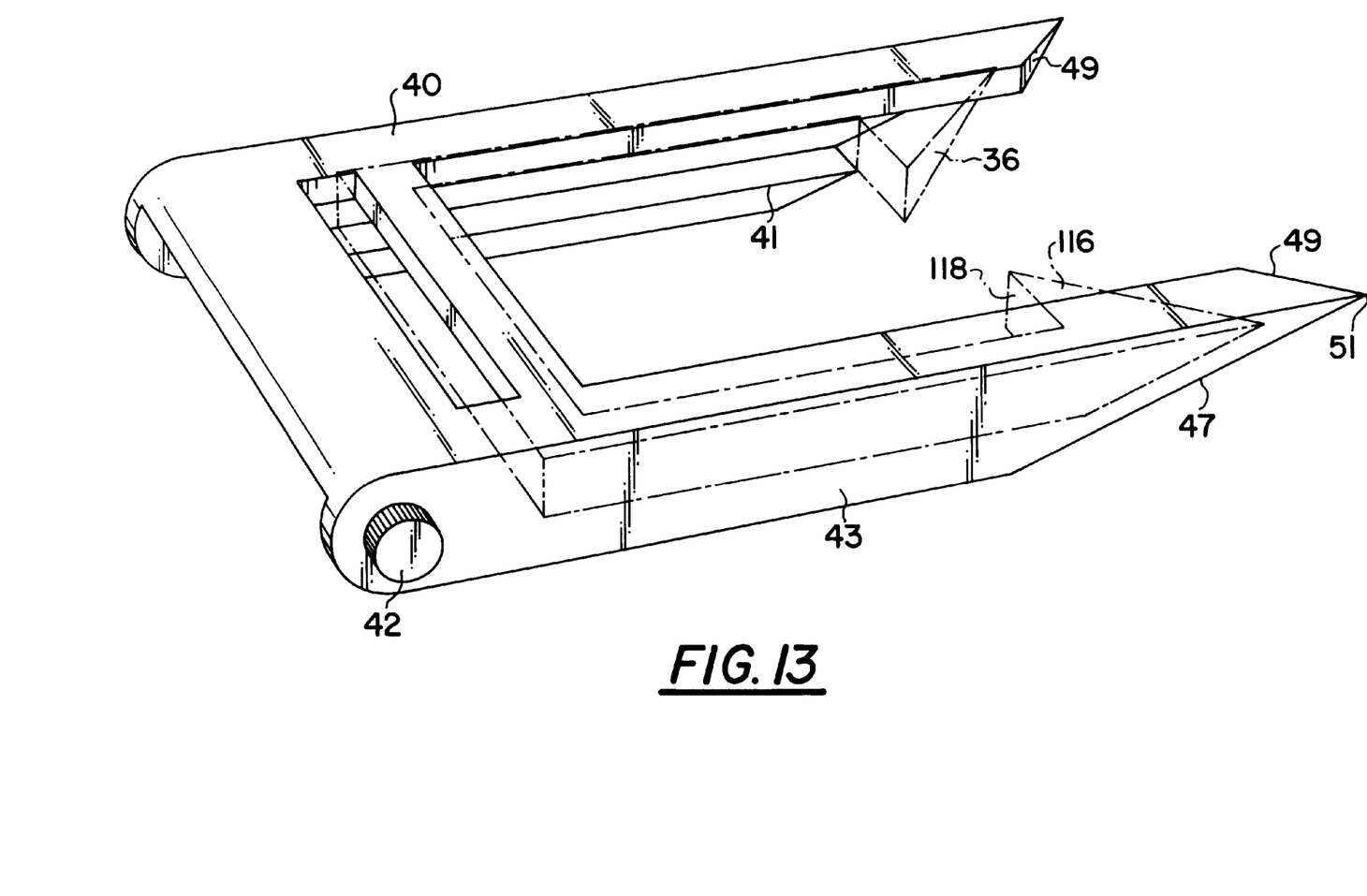
FIG. 13 is an enlarged perspective view of a fastener capsule containing a fastener.

The upper arm assembly 12 has a distal portion 20 extending from the housing assembly 18 and a proximal portion 22 disposed within the housing assembly 18, as shown in FIGS. 2 and 3. The distal portion 20 is of a specific length and width so as to be capable of being inserted into a human nasal passage and to extend, if necessary, along the length of the passage The upper arm assembly 12 includes an upper arm member 24 as shown in FIG. 4. The upper arm member 24 includes an upper arm handle 26 extending from the housing assembly and pivotally coupled to a proximal end thereof at pin 28. The upper arm member 24 includes a pusher assembly 30, comprising a rod 32 biased by spring 34, which biases a series of successive bioabsorbable fasteners 36 towards a distal end of the upper arm member 24. An upper arm actuator or slide 38 is disposed over the upper arm member 24. A distal end of the upper arm slide 38 includes a generally U-shaped fastener capsule 40 pivotally coupled thereto at pin 42. The capsule 40 has surfaces 41 for frictionally holding a fastener 36 therein. As shown in FIG. 13, the capsule 40 has spaced, hollow legs 43, 45. Each leg has a tapered surfaces 47 and 49 which define a sharp cutting tip 51. Thus, the capsule legs 43 and 45 are constructed and arranged to define a trocar, permitting the capsule 40 to pierce or cleanly cut tissue, which facilitates delivery of the fastener to the tissue to be fastened. The upper arm slide 38 further includes a channel 44 extending longitudinally which provides access to the fasteners 36 which are disposed therebelow, the function will become apparent below. A proximal end of the upper arm slide 38 includes a pin 46 biased by spring 48 so as to be slidable within channel 50 (FIG. 4) in a direction transverse to a longitudinal axis of the upper arm slide 38. The pin 46 is connected to a toggle lever 52 of upper handle 54, as will be explained below. The upper arm assembly 12 further includes an upper arm casing 56 which is disposed over the upper arm slide 38. As shown in FIGS. 5 through 8, an underside of the upper arm casing 56 includes a projection 58 separating a pair of leaf springs 60 disposed within channels 61. The leaf springs 60 are mounted so as to be capable of deforming upon contact with the fastener capsule 40, which will become more apparent below.

With reference to FIGS. 2 and 4, a distal end of the toggle lever 52 is coupled to pin 46. A proximal end of the toggle lever 52 is pivotally coupled to the upper handle 54 at pin 62 so as to be movable within recessed portion 64 defined in the upper handle 54. As shown at FIG. 2, the distal end of the upper handle 54 is pivotally coupled to the housing assembly 18 at pin 66. The proximal portion of the upper handle 54 includes a finger-hole 68 for receiving fingers of a user. An underside of the proximal portion of handle 54 is in the form of a generally planar portion 69 which cooperates with a generally planar portion 71 of the upper arm handle 26 so as to move the upper arm handle 26, as will be appreciated below.

Figures 11, 12:
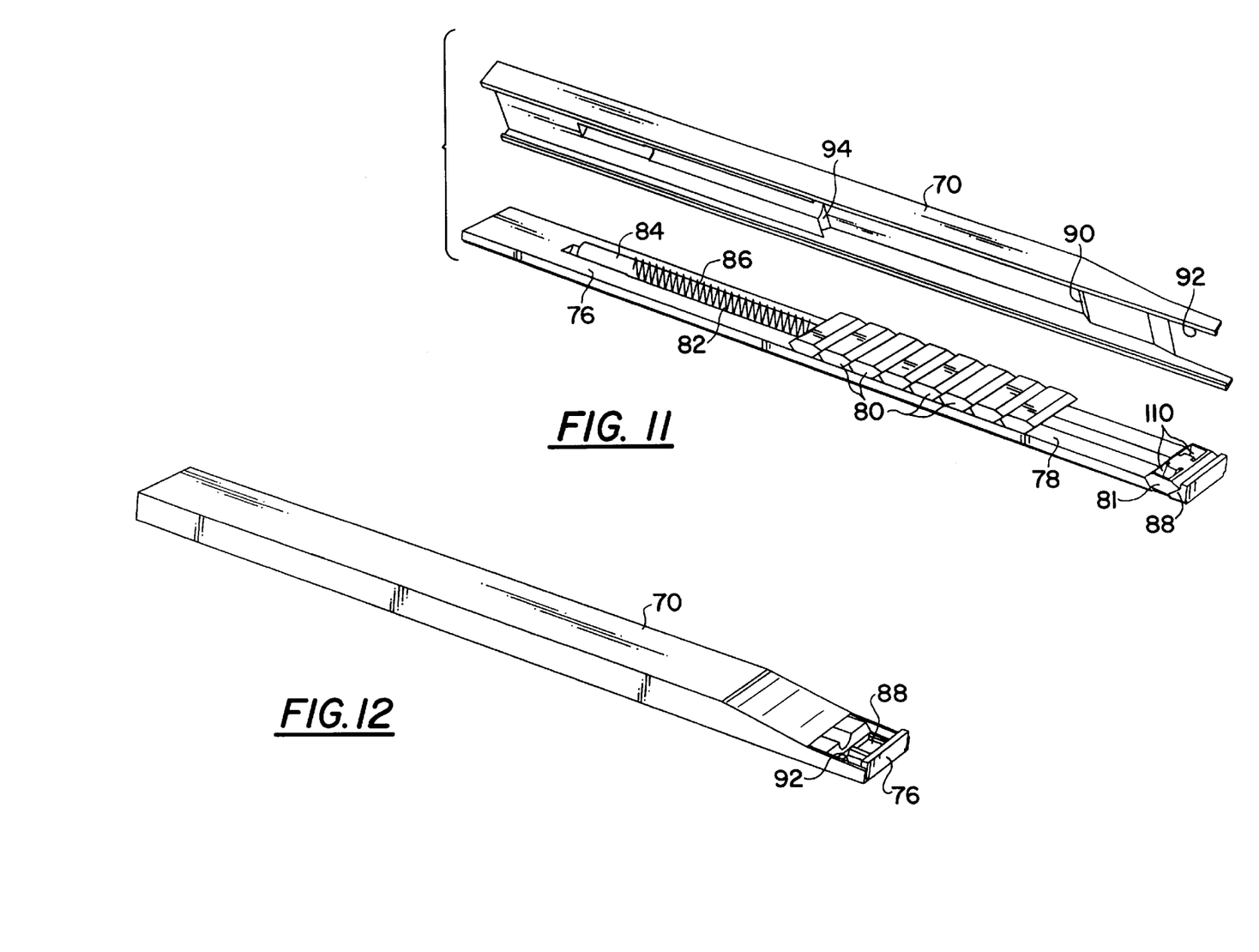
FIG. 11 is an exploded view of a portion of the receptacle arm assembly.
FIG.12 is a perspective view of the receptacle arm assembly of FIG. 11, shown in an assembled condition.

As shown in FIGS. 1 through 4, the receptacle arm assembly 14 of the fastener driving device 10 is pivotally coupled to the upper arm assembly 12 at pivots A and B. The receptacle arm assembly 14 has a distal portion 27 extending from the housing assembly 18 and a proximal portion 29 disposed within the housing assembly 18, as shown in FIGS. 2 and 3. The distal portion 27 is sized and configured substantially identically to the upper arm assembly and is of a specific length and width so as to be capable of being inserted into a human nasal passage and to extend, if necessary, along the length of the passage. The receptacle arm assembly 14 includes a receptacle arm member 70 pivotally connected at pin 74 to a receptacle arm handle 72, which extends from the housing assembly. As shown in FIGS. 4, 11 and 12, the receptacle arm assembly 14 further includes a receptacle actuator or slide 76 which is covered by the receptacle arm member 70. The receptacle slide 76 includes an upper surface 78 for carrying a series of successive bioabsorbable receptacles 80 thereon. The receptacles 80 are spring biased by a pusher assembly 82 comprising a rod 84 and spring 86, as shown in FIG. 11. The distal end of the receptacle slide 76 includes a recessed portion 88 for housing a single, forwardmost receptacle 81 therein. The receptacles 80 are configured identically as shown in FIG. 4. However, FIG. 11 shows the receptacles schematically, to indicate their proper positions. The receptacle arm member 70 includes a stop surface 90, disposed rearwardly of a generally U-shaped open end 92, for preventing the receptacles 80 from moving towards the distal end of the device, and a stop surface 94 for preventing the receptacles 80 from moving towards the proximal end of the device 10.

As shown in FIG. 4, a proximal end of the receptacle slide 76 includes a pin 96 biased by spring 98 and movable within channel 100 transverse to the longitudinal axis of the slide 76. The pin 96 is coupled to a toggle lever 102 of a lower handle 104. The lower handle 104 is pivotally coupled to the housing at pin 105. The lower handle 104 is configured similarly to the upper handle 54, being a mirror image thereof. Planar portion 107 of the receptacle arm handle 72 cooperates with planar portion 109 of the lower handle 104, as will become apparent below.

Figure 1:
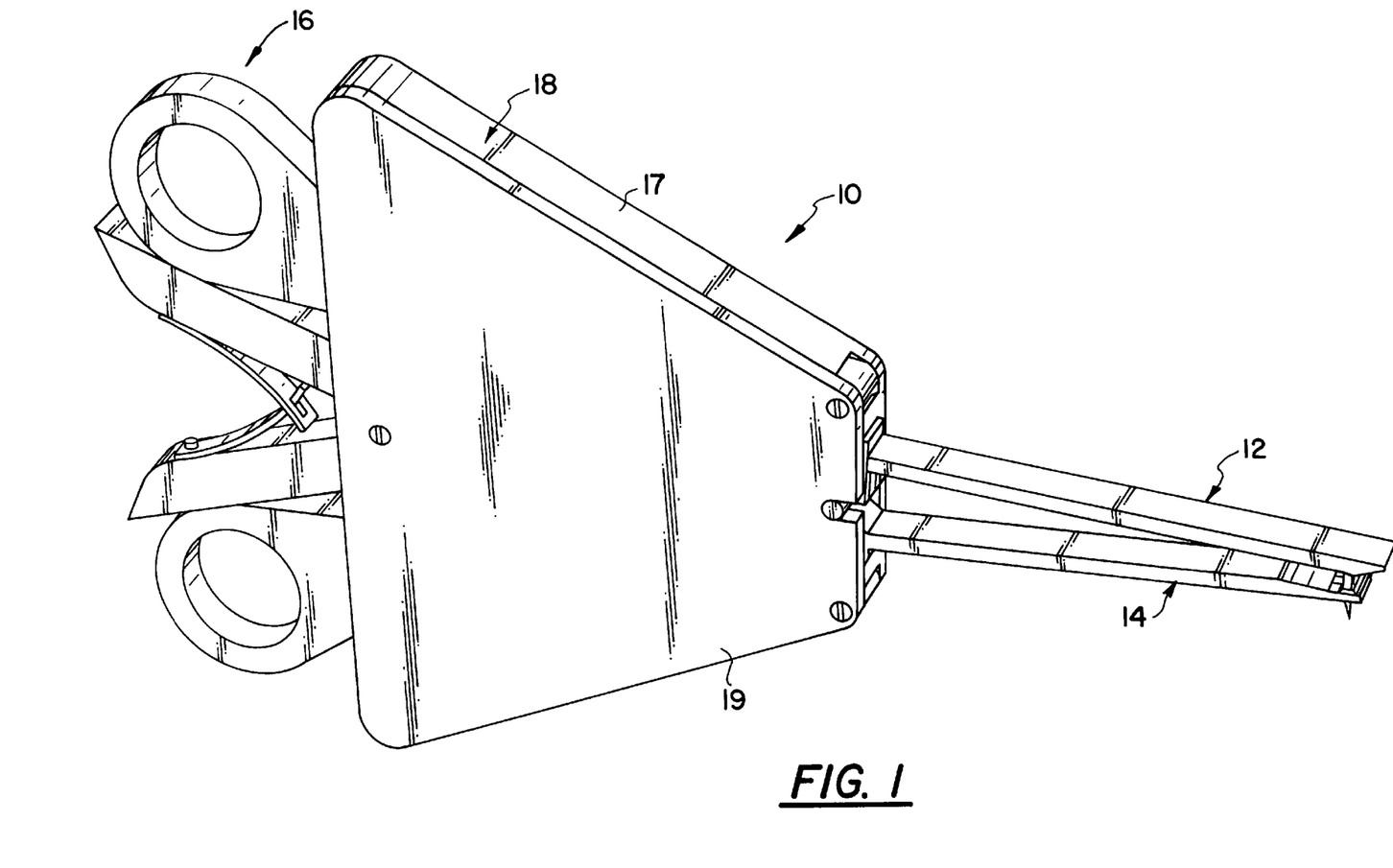
FIG. 1 is a perspective view of the intranasal septal fastener driving device embodying the principles of the present invention.
Figure 10A:
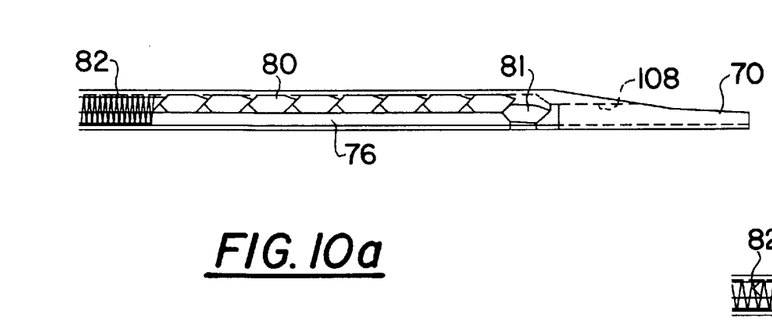
FIGS. 10a and 10b are schematic illustrations of a portion of the receptacle arm assembly for moving a receptacle from an inoperative position to an operative position.

As shown in FIG. 1, a spring 106 is disposed between the upper arm handle 26 and the receptacle arm handle 72 for normally biasing the handles 26, 72 away from each other which in turn biases the upper handle 54 away from the lower handle 104 (FIG. 2). Stop surfaces 111 are defined in the housing assembly 18 for limiting movement of the handles 54 and 104. The upper arm handle 26, the receptacle arm handle 72, the upper handle 54, the lower handle 104 and the spring 106 comprise the handle assembly 16. When the upper and lower handles 54, 104 are biased away from each other, the toggle lever 52 of the upper handle 54 has pivoted in a clockwise direction and has moved the upper arm slide 38 towards the proximal end of the device 10 thereby disposing the fastener capsule 40 in its inoperative position within the upper arm casing 56, shown in FIG. 6. With the lower handle biased in the position shown in FIG. 2, the toggle lever 102 of the lower handle 104 has moved counterclockwise which in turn has moved the receptacle slide 76 towards the proximal end of the device 10, into a position as shown in FIG. 10a. As shown, the recessed distal end of the receptacle slide 76 is in a position so as to receive the leading receptacle 81 of the plurality of receptacles 80.

With reference to the FIGURES, the operation the intranasal fastener driving device 10 of the present invention can be appreciated. As noted above, FIG. 2 shows the fastener driving device 10 in a normally biased, inoperative position, with the upper arm assembly 12 and the receptacle arm assembly 14 in parallel relation. While in the inoperative position, the fastener capsule 40 is in a low profile, inoperative position, with the longitudinal axis of the upper arm assembly 12 and of the capsule 40 being in parallel relation. In this position, the device 10 is moved to the entrance of the nostril with one arm assembly being inserted into one nostril and the other arm assembly being inserted into the other nostril. The upper arm assembly 12 with the fastener capsule 40 in a low profile, inoperative position and the receptacle arm assembly 14 are introduced into the nose and to the desired depth. Handles 54 and 104 are then manually shifted towards each other about pivots 66 and 105, which causes planar portion 69 of the upper handle 54 to engage planar portion 71 of the upper arm handle 26, while planar portion 109 of the lower handle 104 engages the planar portion 107 of the receptacle arm handle 72. This movement causes the distal portions 20, 27 of the arm assemblies 12 and 14 to move towards each other, as will be explained below.

As shown in FIG. 3, the manual movement of the upper and lower handles in turn causes the upper and lower toggle levers, 52 and 102 respectively, to rotate thereby moving the upper arm slide 38 and the receptacle slide 76 in the direction D, as shown in FIG. 3.

Figure 9A:
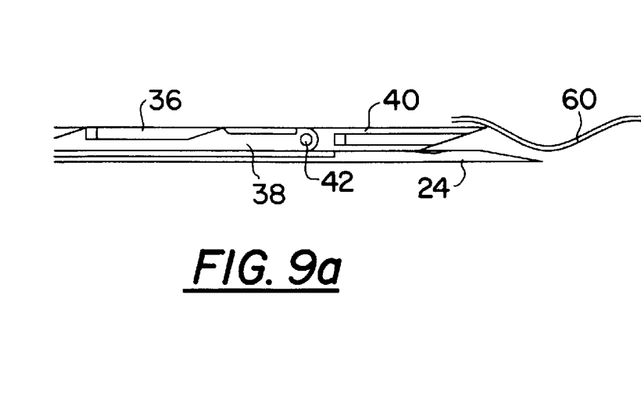
FIGS. 9a and 9b are schematic illustrations indicating the movement of the fastener capsule within the upper arm assembly.
Figure 9B:
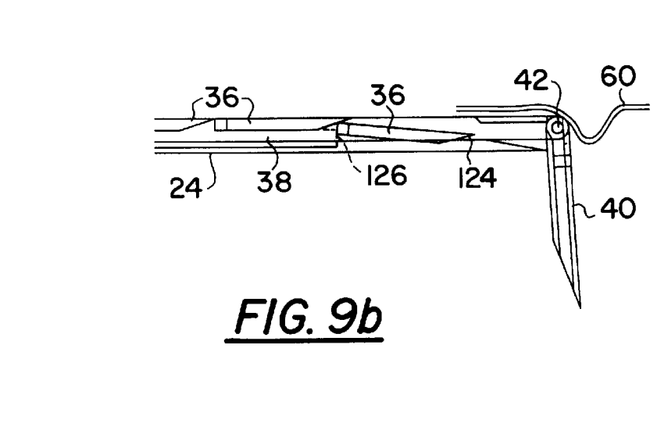

With reference to FIGS. 9a and 9b, the movement of the upper arm slide 38 will be appreciated. As shown in FIG. 9a, the upper arm slide 38 slides along the upper arm member 24. Further movement of the upper arm slide 38 displaces the leaf springs 60 and in turn pushes the tip of the capsule 40 downwardly, as shown in FIG. 9b. As the capsule 40 continues to advance, it fulcrums about the tip of the upper arm member 24. When the end of the capsule 40 is at its final, operative position, the capsule 40 with the leading fastener therein is disposed substantially transversely with respect to a longitudinal axis of the upper arm member 24. The fastener capsule 40 is locked into its operative position due to forward pressure by the upper toggle lever 52 which also keeps the fastener from being pushed back towards the proximal end of the device 10. The capsule 40 then acts as a trocar penetrating the tissue to be fastened.

The leaf springs 60 permit the final forward motion of the capsule 40 due to their flexing and recessing into channels 61 defined in the upper arm casing 56.

Figure 10B:
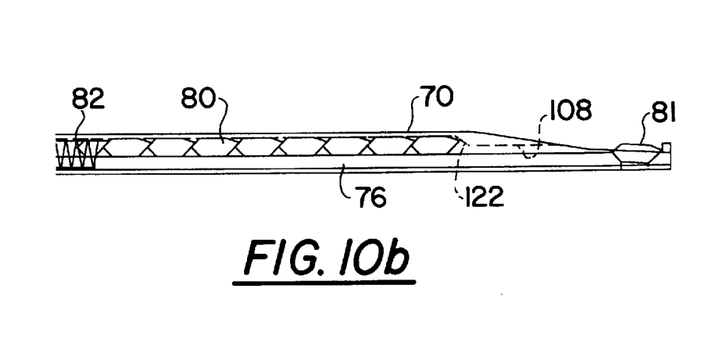
Figure 14:
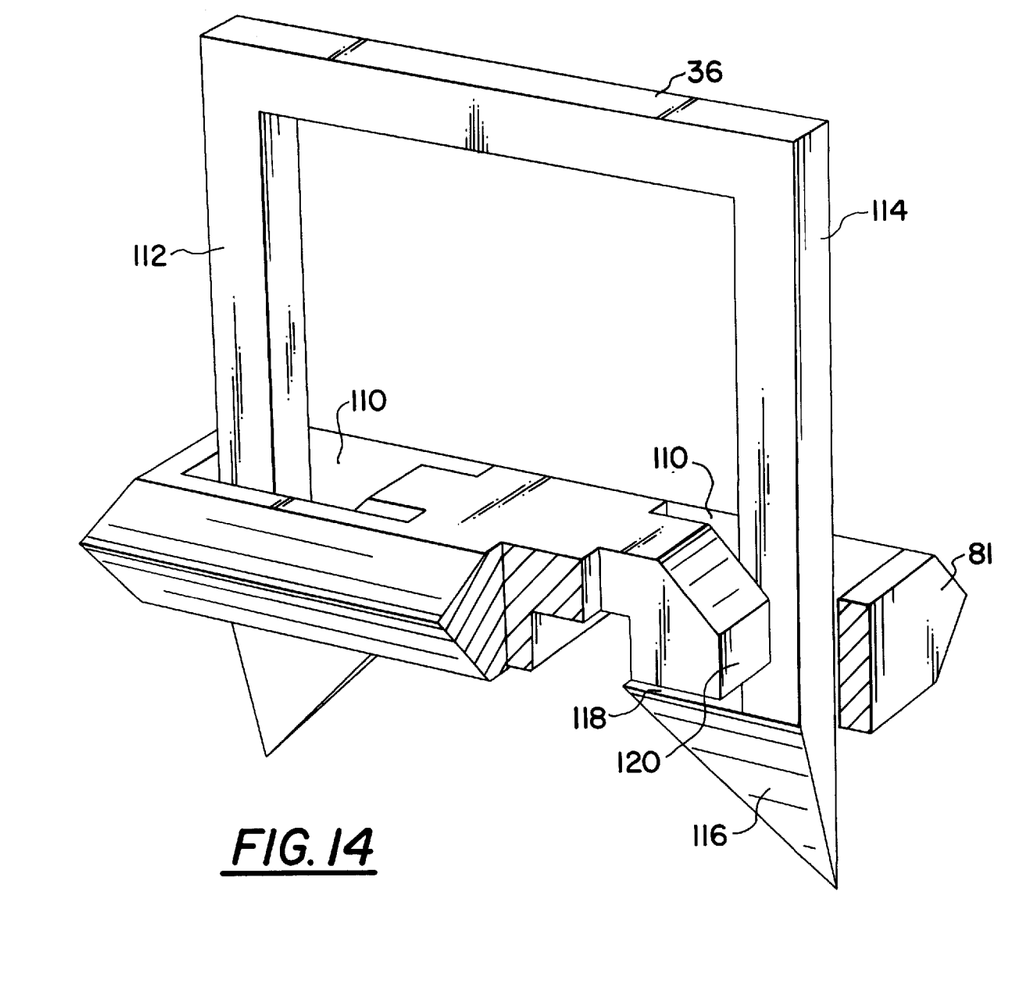
FIG. 14 is an enlarged perspective view, partially in section, showing a fastener engaged with a receptacle.

As shown in FIG. 3, as the upper arm slide 38 is being moved in the direction D, the receptacle slide 76 is moved simultaneously, also in the direction D. With reference to FIG. 10a, the receptacle slide 76, which has received the leading receptacle 81 in recessed portion 88, is moved along channel 108 of the receptacle arm member 70. FIG. 10b shows the receptacle slide 76 moved such that the leading receptacle 81 is disposed in an operative position at the distal end of the receptacle arm assembly 14. The movement of the upper and lower handle members 54 and 104 towards each other causes the upper arm assembly 12 and receptacle arm assembly 14 to perform a scissor motion such that the distal ends of the upper arm assembly and the receptacle arm assembly are moved towards each other. As shown in FIG. 3, the scissor motion occurs since the upper arm assembly 12 is pivotally coupled to the receptacle arm assembly 14 at pivots A and B, such that when the handle members 54 and 104 are moved towards each other, the pivots 28 and 74 move away from each other. As the distal ends of the arm assemblies 12 and 14 are brought towards each other, the ends of a fastener 36 are brought into engagement with bores 110 of the leading receptacle 81. Thus, as shown in FIG. 14, in the preferred embodiment, the fastener 36 is configured so as to have two parallel leg members 112 and 114. Each leg member includes a tapered end 116 having a flange 118 which may be inserted into a respective bore 110 of an associated receptacle. The tapered end 116 of each fastener leg member terminates in a sharp tip which, together with the capsule 40 facilitates cutting tissue during delivery of the fastener 36. Each receptacle 80, 81 includes a flexible flange 120 which is constructed and arranged to bend downwardly, but not backwardly. The flanges 120 holds the fastener 36 in the receptacle and against removal in a direction opposite the direction the fastener has been driven. Thus, the fastener 36 and the receptacles are configured such that the fastener 36 may be inserted easily into the receptacles upon flexing of the flanges 120, but may not be removed easily from the receptacles. The fasteners and receptacles are preferably made of bioabsorbable material so as to be absorbed by the body over time.

During the forward motion of the fastener capsule 40 which carries the leading fastener, the next fastener 36 is pushed via the pusher assembly 30 into a contoured depression 124 in the upper arm member 24, as shown in FIG. 9b. As the empty fastener capsule 40 retracts towards its inoperative position, the next fastener 36 enters the empty core of the capsule 40 and is held therein by friction. Tapered surfaces 47 facilitate picking-up the fastener in the depression 124, permitting the fastener to slide horizontally into the capsule 40. The newly loaded fastener is held posteriorly by a ridge 126 of upper arm member 24 as the capsule 40 and upper arm slide 38 move towards the proximal end of the device. Surface 90 (FIG. 11) of the upper arm member 70 pushes the succeeding row of fasteners back nearly one fastener length as a new fastener is loaded. This completes one fastener driving cycle. The fasteners are designed such that the tapered portion 116 of the succeeding fastener pushes forwardly and downwardly on the fastener which has entered the depression for loading so as to firmly hold it in place.

As shown at FIG. 10b, when a leading receptacle 81 is disposed in its operative position, the remaining receptacles 80 are maintained in an inoperative position since the next receptacle is biased against surface 122 of the receptacle arm member 70. The spring pusher assembly 82 continually biases the receptacles 80 forwardly.

As the upper and lower handles 54, 104 are released, the spring 106 biases the upper arm handle 26 and the receptacle arm handle 72 away from each other thereby biasing the upper and lower handles 54, 104 away from each other until they engage stops 111. This movement causes the upper toggle lever 52 to rotate clockwise so as to move the upper arm slide 38 towards the proximal end of the device thereby returning the fastener capsule 40 to its inoperative position. During this time, the lower toggle lever 102 rotates counterclockwise which in turn moves the receptacle slide 76 towards the proximal portion of the device such that the receptacle slide 76 is disposed in a position as shown in FIG. 10a to receive the leading receptacle 80 within the recessed portion 88 thereof to be ready to be moved to its operative position.

It can be appreciated that the intranasal fastener driving device 10 of the present invention permits relatively large bioabsorbable fasteners to be delivered through a small entrance (the nares), down a narrow passageway to the eventual destination deep within the nose. For increased accuracy, a nasal speculum may be employed which allows direct visualization of the fastening procedure. If cartilage is to be replaced, pockets for insertion of the cartilage can be created and the fastener driving device 10 may be used to secure the cartilage. In addition, tears in the mucosa can be repaired with fasteners and soft tissues grafts for perforation can be accurately anchored with such fastening. Although in the illustrated embodiment, the fastener has two depending legs, it can be appreciated that a single legged fastener can be retained with an associated receptacle.

While the invention has been described in connection with what is presently considered to be the most practical and preferred embodiment, it is to be understood that the invention is not limited to the disclosed embodiment, but, on the contrary, is intended to cover various modifications and equivalent arrangements included within the spirit and scope of the appended claims. For example, although the device has been disclosed for intranasal septal fastening, the device of the invention could be used for fastening other structures during other surgical procedures as well.

What is claimed is:

1. A fastener driving device comprising:

first and second arm assemblies, each of said arm assemblies having a distal portion and a proximal portion, said proximal portion of said first arm assembly being pivotally coupled to said proximal portion of said second arm assembly;

a fastener capsule associated with said first arm assembly and being constructed and arranged at said distal portion thereof so as to receive a leading fastener, said fastener capsule being movable between an inoperative position and an operative position;

a plurality of fasteners carried by said first arm assembly, said fastener capsule being constructed and arranged to individually receive a leading fastener therein, said first arm assembly including a first actuator constructed and arranged to move the fastener capsule from its inoperative position to its operative position;

a plurality of fastener receptacles carried by said second arm assembly, said second arm assembly including a second actuator constructed and arranged to move a leading receptacle of the plurality of receptacles to a position to receive and engage said leading fastener; and a handle assembly coupled to said proximal portions of said first and second arm assemblies, said handle assembly being cooperable with said first actuator such that actuation of said handle assembly (1) moves said fastener capsule with said leading fastener therein from its inoperative position to its operative position and (2) moves said distal portions of said first and second arm assemblies towards each other so as to retain said leading fastener within said leading receptacle.

2. The fastener driving device according to claim 1, wherein said second arm assembly is constructed and arranged to move said leading receptacle from an inoperative position to an operative position at said distal portion of said second arm assembly, said handle assembly being cooperable with said second actuator such that manual actuation of the handle assembly moves said leading receptacle from its inoperative position to its operative position generally simultaneously with the movement of said fastener capsule with said fastener therein from its inoperative position to its operative position.

3. The fastener driving device according to claim 2, further comprising a housing assembly surrounding a portion of said handle assembly and said proximal portions of said first and second arm assemblies, said distal portion of said first and second arm assemblies extending from said housing assembly.

4. The fastener driving device according to claim 3, where said handle assembly comprises:

a first arm handle pivotally coupled to said proximal portion of said first arm assembly and extending therefrom;

a second arm handle pivotally coupled to said proximal portion of said second arm assembly and extending therefrom;

a spring coupled between said first and second arm handles so as to normally bias said first and second arm handles away from each other;

an upper handle member having a distal end and a proximal end, said distal end being pivotally coupled to the housing assembly and said proximal end cooperating with said first arm handle, said upper handle member including an upper toggle lever pivotally coupled thereto at one end thereof, a distal end of said upper toggle lever being coupled to said first actuator;

a lower handle member having a distal end and a proximal end, said distal end of said lower handle member being pivotally coupled to the housing assembly and said proximal end of said lower handle member cooperating with said second arm handle, said lower handle member including a lower toggle lever pivotally coupled thereto at one end thereof, a distal end of said lower toggle lever being coupled to said second actuator, whereby manual movement of said upper and lower handle members moves said first and second arm handles against the bias of said spring causing said distal portions of said first and second arm assemblies to move towards each other while said upper toggle lever rotates with respect to said upper handle member thereby moving said first actuator and thus said fastener capsule with said leading fastener therein from its inoperative position to its operative position and said lower toggle lever rotates with respect to said lower handle member thereby moving said second actuator and thus said leading receptacle from its inoperative position to its operative position.

5. The fastener driving device according to claim 4, wherein said first and second arm handles are pivotally coupled to each other.

6. The fastener driving device according to claim 4, wherein each of said distal ends of said upper and lower handle members include finger-holes for insertion of fingers of a user therein.

7. The fastener driving device according to claim 4, wherein said first arm assembly further includes:

a first arm member having a surface for receiving said plurality of fasteners thereon;

a casing covering said first arm member and being coupled thereto, said casing including biasing structure at a distal end thereof, said first actuator being a slide member disposed between said first arm member and said casing and coupled to said upper toggle lever so as to be movable with respect to said first arm member and said casing, said fastener capsule being pivotally coupled to said slide member such that movement of said slide member as a result of rotation of said upper toggle lever moves said fastener capsule, in its inoperative position, in an axial direction until said fastener capsule contacts said biasing structure, said biasing structure being constructed and arranged to bias said fastener capsule to rotate into its operative position during continued movement of said slide member thereby disposing said fastener capsule generally transversely to said axial direction.

8. The fastener driving device according to claim 7, wherein said first arm member includes a pusher assembly for biasing the plurality of fasteners towards the distal portion of said first arm assembly.

9. The fastener driving device according to claim 7, wherein said biasing structure includes a pair of spaced leaf springs, said fastener capsule having parallel leg members which contact an associated leaf spring during movement of said slide member so as to bias said fastener capsule into its operative position.

10. The fastener driving device according to claim 2, wherein said second actuator is a slide element including a surface for receiving said plurality of receptacles thereon, said second arm assembly further including a receptacle arm member disposed over said slide element such that said slide element is axially movable with respect thereto, said receptacle arm member including a generally U-shaped opened distal end portion, whereby movement of said slide element moves said leading receptacle from its inoperative position into its operative position within the U-shaped distal end portion.

11. The fastener driving device according to claim 10, wherein a distal end of said slide element includes a recessed portion for receiving a receptacle therein.

12. The fastener driving device according to claim 11, wherein said slide element includes a pusher assembly for biasing the plurality of receptacles towards the distal portion of said first arm assembly.

13. The fastener driving device according to claim 1, wherein said fastener capsule is constructed and arranged to frictionally hold a fastener.

14. The fastener driving device according to claim 13, wherein said fastener capsule includes a distal end portion constructed and arranged to define a trocar so as to cut tissue upon movement of the capsule into contact with tissue.

15. The fastener driving device according to claim 14, wherein said distal end portion comprises spaced leg members, each leg member having tapered surfaces which define a sharp cutting tip.

16. The fastener driving device according to claim 1, wherein each fastener includes two parallel leg members, each leg member having a flange at a distal end thereof.

17. The fastener driving device according to claim 16, wherein each receptacle includes first and second spaced bores constructed and arranged to receive the leg members of a fastener, each receptacle including resilient flanges adjacent said bores constructed and arranged to bend upon contact with an associated leg member permitting said associated leg member to enter an associated bore, each flange of said leg members being constructed and arranged to engage an associated resilient flange, said resilient flanges being constructed and arranged to resist bending in a direction opposite to an insertion direction of said leg members to retain said fastener within an associated receptacle.

18. The fastener driving device according to claim 1, wherein said distal portions of said first and second arm assemblies are constructed and arranged to be inserted into associated human nasal passages so as to deliver and retain the leading fastener within nasal tissue.

19. The fastener driving device according to claim 1, where said plurality of fasteners and said plurality of receptacles are bioabsorbable.

20. The fastener driving device according to claim 1, where said plurality of fasteners comprise a series of successive fasteners and said plurality of receptacles comprise a series of successive receptacles.

21. A fastener driving device comprising:

first and second arm assemblies;

a fastener capsule operatively associated with said first arm assembly and being constructed and arranged to be movable between an inoperative position disposed within said first arm assembly and an operative position extending from said first arm assembly;

a plurality of fasteners carried by the said first arm assembly, said fasteners being constructed and arranged to be received individually within said fastener capsule and being provided so as to be successively fed towards said capsule whereby a leading fastener is selectively and sequentially received in said capsule, said first arm assembly including means for moving said fastener capsule between its inoperative and operative positions;

at least one fastener receptacle carried by said second arm assembly, said receptacle being selectively movable to a position to receive and retain said leading fastener; and means for actuating said fastener capsule moving means so as to move said fastener capsule with said leading fastener therein to its operative position, and for moving distal ends of said first and second arm assemblies towards each other, thereby engaging said leading fastener with said receptacle.

22. A fastener driving device comprising:

first and second arm assemblies, each of said arm assemblies having a distal portion and a proximal portion, said proximal portion of said first arm assembly being pivotally coupled to said proximal portion of said second arm assembly;

a fastener capsule associated with said first arm assembly and being constructed and arranged at said distal portion thereof so as to be movable between an inoperative position and an operative position;

a plurality of fasteners carried by said first arm assembly, said fastener capsule being constructed and arranged to individually receive a leading fastener therein, said first arm assembly including a first actuator constructed and arranged to move the fastener capsule from its inoperative position to its operative position;

a plurality of fastener receptacles carried by said second arm assembly, a leading receptacle of the plurality of receptacles being disposed to receive and engage said leading fastener; and a handle assembly coupled to said proximal portions of said first and second arm assemblies, said handle assembly being cooperable with said first actuator such that actuation of said handle assembly (1) moves said fastener capsule with said leading fastener therein from its inoperative position to its operative position and (2) moves said distal portions of said first and second arm assemblies towards each other so as to retain said leading fastener within said leading receptacle, wherein said leading receptacle is movable from an inoperative position to an operative position, said second arm assembly including a second actuator constructed and arranged to move said leading receptacle from an inoperative position to an operative position at said distal portion of said second arm assembly, said handle assembly being cooperable with said second actuator such that manual actuation of the handle assembly moves said leading receptacle from its inoperative position to its inoperative position generally simultaneously with the movement of said fastener capsule with said fastener therein from its inoperative position to its operative position.

* * * * *